United States Patent
Mizrahi et al.

(10) Patent No.: US 8,435,236 B2
(45) Date of Patent: May 7, 2013

(54) TECHNIQUES FOR HEAT-TREATING VARICOSE VEINS

(75) Inventors: Noam Mizrahi, Kfar Vitkin (IL); Shimon Eckhouse, Haifa (IL); Alon Getz, Haifa (IL); Aharon Cohen, Karkur (IL); Fabian Izhack, Kfar Truman (IL); Eran Levit, Kfar Vradim (IL)

(73) Assignee: CardioDex, Ltd., Cesarea Business Park (IL)

( * ) Notice: Subject to any disclaimer, the term of this patent is extended or adjusted under 35 U.S.C. 154(b) by 1169 days.

(21) Appl. No.: 11/791,277

(22) PCT Filed: Nov. 21, 2005

(86) PCT No.: PCT/IB2005/003491
§ 371 (c)(1),
(2), (4) Date: Mar. 12, 2008

(87) PCT Pub. No.: WO2006/054170
PCT Pub. Date: May 26, 2006

(65) Prior Publication Data
US 2008/0167643 A1    Jul. 10, 2008

Related U.S. Application Data

(60) Provisional application No. 60/630,245, filed on Nov. 22, 2004.

(51) Int. Cl.
*A61B 18/18* (2006.01)

(52) U.S. Cl.
USPC .................. 606/31; 606/28; 606/29

(58) Field of Classification Search ............ 606/42, 606/20–41, 49–50; 607/100–102, 115–116
See application file for complete search history.

(56) References Cited

U.S. PATENT DOCUMENTS

| 524,417 A | 8/1894 | Fahey |
| 1,596,004 A | 8/1926 | De Bengoa |

(Continued)

FOREIGN PATENT DOCUMENTS

| BR | 0208039 | 1/2006 |
| BR | PI0208039-7 A | 1/2006 |

(Continued)

OTHER PUBLICATIONS

U.S. Appl. No. 60/630,245, Eckhouse et al.

(Continued)

*Primary Examiner* — Linda Dvorak
*Assistant Examiner* — Brian M Antiskay
(74) *Attorney, Agent, or Firm* — Venable LLP; Michele V. Frank (57) ABSTRACT

An apparatus for treating varicose veins includes a catheter (20) where the distal end is placed within a varicose vein and the proximal portion remains outside the body of the subject. A heating element (22) heats the vein. A cooling element (62) can be applied to an external surface of the skin above the vicinity of the heating element. A control unit (26) can drive the heating element to apply heat to the vein simultaneously. Alternatively, the control unit can apply a current to the heating element to resistively heat a resistive element. A method for treating a varicose vein includes inserting the elongated heating element into the vein, and driving the heating element to apply heat to the segment of vein simultaneously from the entire active heating portion.

14 Claims, 2 Drawing Sheets

U.S. PATENT DOCUMENTS

| | | | |
|---|---|---|---|
| 1,731,069 A | 10/1929 | Herman | |
| 1,881,250 A | 10/1932 | Tomlinson | |
| 1,983,669 A | 12/1934 | Kimble | |
| 2,144,090 A | 1/1939 | Trice | |
| 2,790,442 A | 4/1957 | Donaldson | |
| 2,808,833 A | 10/1957 | August | |
| 3,100,489 A | 8/1963 | Bagley | |
| 3,176,114 A | 3/1965 | Kneisley | |
| 3,301,258 A * | 1/1967 | Werner et al. | 606/50 |
| 3,302,635 A | 2/1967 | Pittman | |
| 3,494,364 A | 2/1970 | Peters | |
| 3,500,828 A | 3/1970 | Podhora | |
| 3,532,095 A | 10/1970 | Miller | |
| 3,595,238 A | 7/1971 | Gavrilov et al. | |
| 3,613,682 A | 10/1971 | Naylor | |
| 3,636,943 A | 1/1972 | Balamuth | |
| 3,699,967 A | 10/1972 | Anderson | |
| 3,794,040 A | 2/1974 | Balamuth | |
| 3,801,766 A | 4/1974 | Morrison, Jr. | |
| 3,801,800 A | 4/1974 | Newton | |
| 3,825,004 A | 7/1974 | Durden, III | |
| 3,858,586 A | 1/1975 | Lessen | |
| 3,874,388 A | 4/1975 | King et al. | |
| 3,886,944 A | 6/1975 | Jamshidi | |
| 3,920,021 A | 11/1975 | Hiltebrandt et al. | |
| 3,929,137 A | 12/1975 | Gonser | |
| 3,938,527 A | 2/1976 | Rioux et al. | |
| 3,963,030 A | 6/1976 | Newton | |
| 3,978,863 A | 9/1976 | Fettel et al. | |
| 3,980,085 A | 9/1976 | Ikuno et al. | |
| 4,003,380 A | 1/1977 | Wien et al. | |
| 4,007,743 A | 2/1977 | Blake | |
| 4,011,872 A | 3/1977 | Komiya et al. | |
| 4,014,343 A | 3/1977 | Esty | |
| 4,016,881 A | 4/1977 | Rioux et al. | |
| 4,043,342 A | 8/1977 | Morrison, Jr. | |
| 4,051,855 A | 10/1977 | Schneiderman | |
| 4,054,143 A | 10/1977 | Bauer et al. | |
| 4,074,718 A | 2/1978 | Morrison, Jr. | |
| 4,112,950 A | 9/1978 | Pike | |
| 4,122,853 A | 10/1978 | Smith | |
| 4,162,673 A | 7/1979 | Patel | |
| 4,168,708 A | 9/1979 | Lepley, Jr. et al. | |
| 4,198,957 A | 4/1980 | Cage et al. | |
| 4,202,337 A | 5/1980 | Hren et al. | |
| 4,211,230 A | 7/1980 | Woltosz | |
| 4,215,699 A | 8/1980 | Patel | |
| 4,228,800 A | 10/1980 | Degler, Jr. et al. | |
| 4,230,119 A | 10/1980 | Blum | |
| 4,269,174 A | 5/1981 | Adair | |
| 4,271,839 A | 6/1981 | Fogarty et al. | |
| 4,271,847 A | 6/1981 | Stokes | |
| 4,273,127 A | 6/1981 | Auth et al. | |
| 4,303,073 A | 12/1981 | Archibald | |
| 4,314,555 A | 2/1982 | Sagae et al. | |
| 4,314,559 A | 2/1982 | Allen | |
| 4,317,445 A | 3/1982 | Robinson | |
| 4,327,709 A | 5/1982 | Hanson et al. | |
| 4,352,924 A | 10/1982 | Wooten et al. | |
| 4,353,371 A | 10/1982 | Cosman | |
| 4,359,052 A | 11/1982 | Staub | |
| 4,364,392 A | 12/1982 | Strother et al. | |
| 4,370,980 A | 2/1983 | Lottick | |
| 4,390,018 A | 6/1983 | Zukowski | |
| 4,404,971 A | 9/1983 | LeVeen et al. | |
| 4,411,266 A | 10/1983 | Cosman | |
| 4,418,692 A | 12/1983 | Guay | |
| 4,424,833 A | 1/1984 | Spector et al. | |
| 4,470,415 A | 9/1984 | Wozniak | |
| 4,476,862 A | 10/1984 | Pao | |
| 4,481,057 A | 11/1984 | Beard | |
| 4,483,338 A | 11/1984 | Bloom et al. | |
| 4,492,231 A | 1/1985 | Auth | |
| 4,498,475 A | 2/1985 | Schneiderman | |
| 4,520,823 A | 6/1985 | LeVeen et al. | |
| 4,522,205 A | 6/1985 | Taylor et al. | |
| 4,532,924 A | 8/1985 | Auth et al. | |
| 4,539,987 A | 9/1985 | Nath et al. | |
| 4,548,207 A | 10/1985 | Reimels | |
| 4,625,724 A | 12/1986 | Suzuki et al. | |
| 4,637,392 A | 1/1987 | Sorochenko et al. | |
| 4,645,491 A | 2/1987 | Evans et al. | |
| 4,654,024 A | 3/1987 | Crittenden et al. | |
| 4,671,274 A | 6/1987 | Sorochenko et al. | |
| 4,672,969 A | 6/1987 | Dew | |
| 4,682,596 A | 7/1987 | Bales et al. | |
| 4,708,136 A | 11/1987 | Saito | |
| 4,709,698 A | 12/1987 | Johnston et al. | |
| 4,716,897 A | 1/1988 | Noguchi et al. | |
| 4,717,381 A | 1/1988 | Papantonakos et al. | |
| 4,735,201 A | 4/1988 | O'Reilly | |
| 4,744,359 A | 5/1988 | Hatta et al. | |
| 4,744,364 A | 5/1988 | Kensey | |
| 4,760,847 A | 8/1988 | Vaillancourt | |
| 4,765,331 A | 8/1988 | Petruzzi et al. | |
| 4,776,349 A | 10/1988 | Nashef et al. | |
| 4,790,819 A | 12/1988 | Li et al. | |
| 4,801,293 A | 1/1989 | Jackson | |
| 4,832,688 A | 5/1989 | Sagae et al. | |
| 4,834,725 A | 5/1989 | Iwatschenko et al. | |
| 4,836,204 A | 6/1989 | Landymore et al. | |
| 4,848,337 A | 7/1989 | Shaw et al. | |
| 4,848,339 A | 7/1989 | Rink et al. | |
| 4,848,352 A | 7/1989 | Pohndorf et al. | |
| 4,850,960 A | 7/1989 | Grayzel | |
| 4,852,568 A | 8/1989 | Kensey | |
| 4,854,320 A | 8/1989 | Dew et al. | |
| 4,860,745 A | 8/1989 | Farin et al. | |
| 4,869,248 A | 9/1989 | Narula | |
| 4,890,612 A | 1/1990 | Kensey | |
| 4,900,303 A | 2/1990 | Lemelson | |
| 4,917,089 A | 4/1990 | Sideris | |
| 4,920,980 A | 5/1990 | Jackowski | |
| 4,921,478 A | 5/1990 | Solano et al. | |
| 4,929,246 A | 5/1990 | Sinofsky | |
| 4,938,761 A | 7/1990 | Ensslin | |
| 4,943,290 A | 7/1990 | Rexroth et al. | |
| 4,946,463 A | 8/1990 | Wright | |
| 4,953,559 A | 9/1990 | Salerno et al. | |
| 4,960,133 A | 10/1990 | Hewson | |
| 4,961,729 A | 10/1990 | Vaillancourt | |
| 4,979,948 A | 12/1990 | Geddes et al. | |
| 4,994,060 A | 2/1991 | Rink et al. | |
| 5,002,051 A | 3/1991 | Dew et al. | |
| 5,006,119 A | 4/1991 | Acker et al. | |
| 5,009,656 A | 4/1991 | Reimels | |
| 5,013,312 A | 5/1991 | Parins et al. | |
| 5,021,059 A | 6/1991 | Kensey et al. | |
| 5,035,695 A | 7/1991 | Weber, Jr. et al. | |
| 5,038,789 A | 8/1991 | Frazin | |
| 5,047,025 A | 9/1991 | Taylor et al. | |
| 5,047,028 A | 9/1991 | Qian et al. | |
| 5,049,148 A | 9/1991 | Mehl | |
| 5,053,046 A | 10/1991 | Janese | |
| 5,057,105 A | 10/1991 | Malone et al. | |
| 5,061,267 A | 10/1991 | Zeiher et al. | |
| 5,061,274 A | 10/1991 | Kensey | |
| 5,073,166 A | 12/1991 | Parks et al. | |
| 5,078,743 A | 1/1992 | Mikalov et al. | |
| 5,080,660 A | 1/1992 | Buelna | |
| 5,085,659 A | 2/1992 | Rydell | |
| 5,087,256 A | 2/1992 | Taylor et al. | |
| 5,088,997 A | 2/1992 | Delahuerga et al. | |
| 5,103,804 A | 4/1992 | Abele et al. | |
| 5,108,392 A | 4/1992 | Spingler et al. | |
| 5,108,420 A | 4/1992 | Marks | |
| 5,108,421 A | 4/1992 | Fowler | |
| RE33,925 E | 5/1992 | Bales et al. | |
| 5,116,332 A | 5/1992 | Lottick | |
| 5,122,137 A | 6/1992 | Lennox | |
| 5,122,139 A | 6/1992 | Sutter et al. | |
| 5,129,882 A | 7/1992 | Weldon et al. | |
| 5,131,394 A | 7/1992 | Gehlbach | |
| 5,133,714 A | 7/1992 | Beane | |
| 5,141,515 A | 8/1992 | Eberbach | |
| 5,147,316 A | 9/1992 | Castillenti | |
| 5,147,357 A | 9/1992 | Rose et al. | |

| | | | | | | |
|---|---|---|---|---|---|---|
| 5,151,098 A | 9/1992 | Loertscher et al. | 5,728,133 A | 3/1998 | Kontos | |
| 5,151,102 A | 9/1992 | Kamiyama et al. | 5,728,134 A | 3/1998 | Barak | |
| 5,156,613 A | 10/1992 | Sawyer | 5,746,755 A | 5/1998 | Wood et al. | |
| 5,158,561 A | 10/1992 | Rydell et al. | 5,782,860 A | 7/1998 | Epstein et al. | |
| 5,159,925 A | 11/1992 | Neuwirth et al. | 5,782,861 A | 7/1998 | Cragg et al. | |
| 5,178,620 A | 1/1993 | Eggers et al. | 5,810,810 A | 9/1998 | Tay et al. | |
| 5,183,464 A | 2/1993 | Dubrul et al. | 5,836,945 A | 11/1998 | Perkins | |
| 5,188,602 A | 2/1993 | Nichols | 5,853,421 A | 12/1998 | Leschinsky et al. | |
| 5,188,634 A | 2/1993 | Hussein et al. | 5,868,778 A | 2/1999 | Gershony et al. | |
| 5,190,541 A | 3/1993 | Abele et al. | 5,879,499 A | 3/1999 | Corvi | |
| 5,192,300 A | 3/1993 | Fowler | 5,891,138 A | 4/1999 | Tu et al. | |
| 5,192,302 A | 3/1993 | Kensey et al. | 5,895,386 A | 4/1999 | Odell et al. | |
| 5,207,675 A | 5/1993 | Canady | 5,906,636 A | 5/1999 | Casscells, III et al. | |
| 5,211,624 A | 5/1993 | Cinberg et al. | 5,911,719 A | 6/1999 | Eggers | |
| 5,215,103 A | 6/1993 | Desai | 5,922,009 A | 7/1999 | Epstein et al. | |
| 5,217,024 A | 6/1993 | Dorsey et al. | 5,928,266 A | 7/1999 | Kontos | |
| 5,217,451 A | 6/1993 | Freitas | 5,941,897 A | 8/1999 | Myers | |
| 5,217,458 A | 6/1993 | Parins | 5,944,730 A | 8/1999 | Nobles et al. | |
| 5,217,459 A | 6/1993 | Kamerling | 5,951,589 A | 9/1999 | Epstein et al. | |
| 5,217,460 A | 6/1993 | Knoepfler | 5,964,782 A | 10/1999 | Lafontaine et al. | |
| 5,220,924 A | 6/1993 | Frazin | 5,984,950 A | 11/1999 | Cragg et al. | |
| 5,221,259 A | 6/1993 | Weldon et al. | 6,002,361 A | 12/1999 | Schipper | |
| 5,221,281 A | 6/1993 | Klicek | 6,007,563 A | 12/1999 | Nash et al. | |
| 5,222,974 A | 6/1993 | Kensey et al. | 6,022,336 A | 2/2000 | Zadno-Azizi et al. | |
| 5,226,908 A | 7/1993 | Yoon | 6,022,361 A | 2/2000 | Epstein et al. | |
| 5,230,349 A | 7/1993 | Langberg | 6,033,398 A * | 3/2000 | Farley et al. | 606/27 |
| 5,257,635 A | 11/1993 | Langberg | 6,033,401 A | 3/2000 | Edwards et al. | |
| 5,258,000 A | 11/1993 | Gianturco | 6,045,569 A | 4/2000 | Kensey et al. | |
| 5,258,006 A | 11/1993 | Rydell et al. | 6,048,358 A | 4/2000 | Barak | |
| 5,269,780 A | 12/1993 | Roos et al. | 6,056,768 A | 5/2000 | Cates et al. | |
| 5,275,616 A | 1/1994 | Fowler | 6,056,769 A | 5/2000 | Epstein et al. | |
| 5,277,696 A | 1/1994 | Hagen et al. | 6,063,085 A | 5/2000 | Tay et al. | |
| 5,281,216 A | 1/1994 | Klicek | 6,071,277 A | 6/2000 | Farley et al. | |
| 5,282,799 A | 2/1994 | Rydell | 6,071,300 A | 6/2000 | Brenneman et al. | |
| 5,282,827 A | 2/1994 | Kensey et al. | 6,080,183 A | 6/2000 | Tsugita et al. | |
| 5,290,310 A | 3/1994 | Makower et al. | 6,090,130 A | 7/2000 | Nash et al. | |
| 5,292,332 A | 3/1994 | Lee | 6,104,291 A | 8/2000 | Beauvillier et al. | |
| 5,304,117 A | 4/1994 | Wilk | 6,111,424 A | 8/2000 | Bosacchi | |
| 5,304,214 A | 4/1994 | DeFord et al. | 6,113,598 A | 9/2000 | Baker | |
| 5,306,254 A | 4/1994 | Nash et al. | 6,120,524 A | 9/2000 | Taheri | |
| 5,320,639 A | 6/1994 | Rudnick | 6,126,635 A | 10/2000 | Simpson et al. | |
| 5,324,306 A | 6/1994 | Makower et al. | 6,142,994 A | 11/2000 | Swanson et al. | |
| 5,342,359 A | 8/1994 | Rydell | 6,152,920 A | 11/2000 | Thompson et al. | |
| 5,342,393 A | 8/1994 | Stack | 6,179,832 B1 | 1/2001 | Jones et al. | |
| 5,349,166 A | 9/1994 | Taylor | 6,217,574 B1 | 4/2001 | Webster | |
| 5,364,389 A | 11/1994 | Anderson | 6,228,082 B1 | 5/2001 | Baker et al. | |
| 5,370,660 A | 12/1994 | Weinstein et al. | 6,235,027 B1 | 5/2001 | Herzon | |
| 5,383,896 A | 1/1995 | Gershony et al. | 6,267,758 B1 | 7/2001 | Daw et al. | |
| 5,383,899 A | 1/1995 | Hammerslag | 6,287,322 B1 | 9/2001 | Zhu et al. | |
| 5,411,520 A | 5/1995 | Nash et al. | 6,306,133 B1 | 10/2001 | Tu et al. | |
| 5,413,571 A | 5/1995 | Katsaros et al. | 6,315,787 B1 | 11/2001 | Tsugita et al. | |
| 5,415,657 A | 5/1995 | Taymor-Luria | 6,322,559 B1 | 11/2001 | Daulton et al. | |
| 5,417,689 A | 5/1995 | Fine | 6,350,274 B1 | 2/2002 | Li | |
| 5,419,195 A | 5/1995 | Quinn | 6,352,533 B1 | 3/2002 | Ellman et al. | |
| 5,419,765 A | 5/1995 | Weldon et al. | 6,368,341 B1 | 4/2002 | Abrahamson | |
| 5,431,639 A | 7/1995 | Shaw | 6,371,964 B1 | 4/2002 | Vargas et al. | |
| 5,437,631 A | 8/1995 | Janzen et al. | 6,371,974 B1 | 4/2002 | Brenneman et al. | |
| 5,441,517 A | 8/1995 | Kensey et al. | 6,398,780 B1 | 6/2002 | Farley et al. | |
| 5,454,833 A | 10/1995 | Boussignac et al. | 6,398,782 B1 | 6/2002 | Pecor et al. | |
| 5,458,573 A | 10/1995 | Summers | 6,402,745 B1 | 6/2002 | Wilk | |
| 5,486,195 A | 1/1996 | Myers et al. | 6,409,739 B1 | 6/2002 | Nobles et al. | |
| 5,507,744 A | 4/1996 | Tay et al. | 6,443,947 B1 | 9/2002 | Marko et al. | |
| 5,540,715 A | 7/1996 | Katsaros et al. | 6,450,989 B2 | 9/2002 | Dubrul et al. | |
| RE35,330 E | 9/1996 | Malone et al. | 6,451,007 B1 * | 9/2002 | Koop et al. | 606/9 |
| 5,593,406 A | 1/1997 | Eggers et al. | 6,468,272 B1 | 10/2002 | Koblish et al. | |
| 5,611,798 A | 3/1997 | Eggers | 6,482,179 B1 | 11/2002 | Chu et al. | |
| 5,624,452 A | 4/1997 | Yates | 6,503,247 B2 | 1/2003 | Swartz et al. | |
| 5,626,601 A | 5/1997 | Gershony et al. | 6,508,828 B1 | 1/2003 | Akerfeldt et al. | |
| 5,630,833 A | 5/1997 | Katsaros et al. | 6,511,479 B2 | 1/2003 | Gentelia et al. | |
| 5,645,566 A | 7/1997 | Brenneman et al. | 6,512,458 B1 | 1/2003 | Kobayashi et al. | |
| 5,654,566 A | 8/1997 | Johnson | 6,529,756 B1 | 3/2003 | Phan et al. | |
| 5,676,689 A | 10/1997 | Kensey et al. | 6,533,778 B2 | 3/2003 | Herzon | |
| 5,700,277 A | 12/1997 | Nash et al. | 6,537,299 B1 | 3/2003 | Hogendijk et al. | |
| 5,702,387 A | 12/1997 | Arts et al. | 6,551,313 B1 | 4/2003 | Levin | |
| 5,716,325 A | 2/1998 | Bonutti | 6,569,161 B2 | 5/2003 | Zappala | |
| 5,716,375 A | 2/1998 | Fowler | 6,569,182 B1 | 5/2003 | Balceta et al. | |
| RE35,755 E | 3/1998 | Qian | 6,589,237 B2 | 7/2003 | Woloszko et al. | |
| 5,725,551 A | 3/1998 | Myers et al. | 6,593,853 B1 | 7/2003 | Barrett et al. | |
| 5,728,122 A | 3/1998 | Leschinsky et al. | 6,626,899 B2 | 9/2003 | Houser et al. | |

| | | |
|---|---|---|
| 6,626,901 B1 | 9/2003 | Treat et al. |
| 6,656,136 B1 | 12/2003 | Weng et al. |
| 6,656,207 B2 | 12/2003 | Epstein et al. |
| 6,657,447 B1 | 12/2003 | Parandoosh |
| 6,676,657 B2 | 1/2004 | Wood |
| 6,676,685 B2 | 1/2004 | Pedros et al. |
| 6,679,904 B2 | 1/2004 | Gleeson et al. |
| 6,682,526 B1 | 1/2004 | Jones et al. |
| 6,689,126 B1 | 2/2004 | Farley et al. |
| 6,699,262 B2 | 3/2004 | Redmond et al. |
| 6,712,804 B2 | 3/2004 | Roue et al. |
| 6,712,806 B2 | 3/2004 | St. Germain et al. |
| 6,712,815 B2 | 3/2004 | Sampson et al. |
| 6,719,257 B1 | 4/2004 | Greene et al. |
| 6,743,195 B2 | 6/2004 | Zucker |
| 6,768,086 B2 | 7/2004 | Sullivan et al. |
| 6,772,013 B1 | 8/2004 | Ingle et al. |
| 6,780,177 B2 | 8/2004 | Shafirstein et al. |
| 6,814,743 B2 | 11/2004 | Chin et al. |
| 6,817,743 B2 | 11/2004 | Sharper |
| 6,840,666 B2 | 1/2005 | Enachescu et al. |
| 6,846,321 B2 | 1/2005 | Zucker |
| 6,860,880 B2 | 3/2005 | Treat et al. |
| 6,904,303 B2 | 6/2005 | Phan et al. |
| 6,908,463 B2 | 6/2005 | Treat et al. |
| 6,932,810 B2 | 8/2005 | Ryan |
| 6,939,363 B2 | 9/2005 | Åkerfeldt et al. |
| 6,942,674 B2 | 9/2005 | Belef et al. |
| 6,960,206 B2 | 11/2005 | Keane |
| 6,969,397 B2 | 11/2005 | Ginn |
| 6,984,219 B2 | 1/2006 | Ashby et al. |
| 6,997,926 B2 | 2/2006 | Gellman et al. |
| 7,001,398 B2 | 2/2006 | Carley et al. |
| 7,008,441 B2 | 3/2006 | Zucker et al. |
| 7,025,748 B2 | 4/2006 | Ashby |
| 7,029,489 B1 | 4/2006 | Ashby et al. |
| 7,033,352 B1 | 4/2006 | Gauthier et al. |
| 7,037,322 B1 | 5/2006 | Sing et al. |
| 7,070,597 B2 | 7/2006 | Truckai et al. |
| 7,073,509 B2 | 7/2006 | Tenerz et al. |
| 7,099,717 B2 | 8/2006 | Woodard et al. |
| 7,115,127 B2 | 10/2006 | Lindenbaum et al. |
| 7,144,411 B2 | 12/2006 | Ginn et al. |
| 7,147,634 B2 | 12/2006 | Nesbitt |
| 7,151,442 B1 | 12/2006 | Nguyen |
| 7,153,301 B2 | 12/2006 | Swartz et al. |
| 7,154,283 B1 | 12/2006 | Weakley et al. |
| 7,160,297 B2 | 1/2007 | Nesbitt |
| 7,164,353 B2 | 1/2007 | Puleston et al. |
| 7,175,646 B2 | 2/2007 | Brenneman et al. |
| 7,184,811 B2 | 2/2007 | Phan et al. |
| 7,201,725 B1 | 4/2007 | Cragg et al. |
| 7,211,080 B2 | 5/2007 | Treat et al. |
| 7,223,266 B2 | 5/2007 | Lindenbaum et al. |
| 7,225,992 B2 | 6/2007 | Forster |
| 7,257,450 B2 | 8/2007 | Auth et al. |
| 7,474,909 B2 | 1/2009 | Phan et al. |
| 7,850,685 B2 | 12/2010 | Kunis et al. |
| 2001/0003158 A1 | 6/2001 | Kensey et al. |
| 2001/0007070 A1 | 7/2001 | Stewart et al. |
| 2001/0029373 A1 | 10/2001 | Baker et al. |
| 2002/0002371 A1 | 1/2002 | Acker et al. |
| 2002/0022822 A1 | 2/2002 | Cragg et al. |
| 2002/0062130 A1 | 5/2002 | Jugenheimer et al. |
| 2002/0072761 A1 | 6/2002 | Abrams et al. |
| 2002/0133123 A1 | 9/2002 | Zucker |
| 2002/0156495 A1 | 10/2002 | Brenneman et al. |
| 2002/0193808 A1 | 12/2002 | Belef et al. |
| 2003/0005397 A1 | 1/2003 | Larsen |
| 2003/0055397 A1 | 3/2003 | Zucker |
| 2003/0055454 A1 | 3/2003 | Zucker |
| 2003/0093116 A1 | 5/2003 | Nowakowski |
| 2003/0109869 A1 | 6/2003 | Shadduck |
| 2003/0120256 A1 | 6/2003 | Lary et al. |
| 2003/0125766 A1 | 7/2003 | Ding |
| 2003/0153060 A1 | 8/2003 | Wilson et al. |
| 2003/0191479 A1 | 10/2003 | Thornton |
| 2003/0195498 A1 | 10/2003 | Treat et al. |
| 2003/0199863 A1 | 10/2003 | Swanson et al. |
| 2003/0236518 A1 | 12/2003 | Marchitto et al. |
| 2004/0006333 A1 | 1/2004 | Arnold et al. |
| 2004/0010298 A1 | 1/2004 | Altshuler et al. |
| 2004/0030348 A1 | 2/2004 | Peterson et al. |
| 2004/0068306 A1 | 4/2004 | Shadduck |
| 2004/0092913 A1* | 5/2004 | Hennings et al. ............. 606/3 |
| 2004/0102797 A1 | 5/2004 | Golden et al. |
| 2004/0153054 A1 | 8/2004 | Lindenbaum et al. |
| 2004/0153060 A1 | 8/2004 | Lindenbaum et al. |
| 2004/0158287 A1 | 8/2004 | Cragg et al. |
| 2004/0199155 A1 | 10/2004 | Mollenauer |
| 2004/0199226 A1 | 10/2004 | Shadduck |
| 2004/0215232 A1 | 10/2004 | Belhe et al. |
| 2004/0220562 A1* | 11/2004 | Garabedian et al. ............ 606/41 |
| 2004/0249324 A1 | 12/2004 | Louis |
| 2004/0249342 A1 | 12/2004 | Khosravi et al. |
| 2004/0267307 A1 | 12/2004 | Bagaoisan et al. |
| 2005/0038419 A9 | 2/2005 | Arnold et al. |
| 2005/0085854 A1 | 4/2005 | Ginn |
| 2005/0192654 A1 | 9/2005 | Chanduszko et al. |
| 2005/0209637 A1 | 9/2005 | Zhu et al. |
| 2005/0228443 A1 | 10/2005 | Yassinzadeh |
| 2005/0267522 A1 | 12/2005 | Yassinzadeh et al. |
| 2005/0273095 A1 | 12/2005 | Taimisto et al. |
| 2005/0277980 A1 | 12/2005 | Yassinzadeh |
| 2006/0089637 A1 | 4/2006 | Werneth et al. |
| 2006/0190066 A1* | 8/2006 | Worthen ...................... 607/105 |
| 2006/0206121 A1 | 9/2006 | Chin et al. |
| 2006/0235376 A1 | 10/2006 | Lindenbaum et al. |
| 2006/0253072 A1 | 11/2006 | Pai et al. |
| 2006/0271032 A1 | 11/2006 | Chin et al. |
| 2006/0276836 A1 | 12/2006 | Bergin et al. |
| 2007/0010391 A1 | 1/2007 | Mikijelj et al. |
| 2007/0021746 A1 | 1/2007 | Taimisto et al. |
| 2007/0021770 A1 | 1/2007 | Brenneman et al. |
| 2007/0049968 A1 | 3/2007 | Sibbitt et al. |
| 2007/0100232 A1 | 5/2007 | Hiller et al. |
| 2007/0198057 A1 | 8/2007 | Gelbart et al. |
| 2007/0208330 A1 | 9/2007 | Treat et al. |
| 2007/0213710 A1 | 9/2007 | Lindenbaum et al. |
| 2007/0233185 A1 | 10/2007 | Anderson et al. |
| 2007/0282975 A1 | 12/2007 | Kato |
| 2008/0009747 A1 | 1/2008 | Saadat et al. |
| 2008/0015569 A1 | 1/2008 | Saadat et al. |
| 2008/0039793 A1 | 2/2008 | Goldman et al. |
| 2008/0039829 A1 | 2/2008 | Goldman et al. |
| 2008/0065150 A1 | 3/2008 | Drasler et al. |
| 2008/0082122 A1 | 4/2008 | Khosravi et al. |
| 2008/0091193 A1 | 4/2008 | Kauphusman et al. |
| 2008/0154303 A1 | 6/2008 | Yassinzadeh |
| 2008/0167643 A1 | 7/2008 | Mizrahi et al. |
| 2008/0177300 A1 | 7/2008 | Mas et al. |
| 2009/0125056 A1 | 5/2009 | Buchbinder et al. |
| 2009/0149847 A1 | 6/2009 | Yadin et al. |
| 2009/0163903 A1 | 6/2009 | Lindenbaum et al. |
| 2010/0228241 A1 | 9/2010 | Eckhouse et al. |

FOREIGN PATENT DOCUMENTS

| | | |
|---|---|---|
| CA | 2514865 A1 | 8/2004 |
| CA | 2587228 A1 | 5/2006 |
| DK | 1096884 A | 5/2005 |
| EP | 1096884 B1 | 5/2001 |
| EP | 1368089 A1 | 12/2003 |
| EP | 1599239 A2 | 11/2005 |
| EP | 1711117 B1 | 10/2006 |
| JP | 3-080847 A | 4/1991 |
| JP | 5-337131 A | 12/1993 |
| JP | 6-233779 A | 8/1994 |
| JP | 8-501947 A | 3/1996 |
| JP | 2001-190561 A | 7/2001 |
| JP | 2002-301088 A | 10/2002 |
| JP | 2003-067676 A | 3/2003 |
| JP | 200322074 | 8/2003 |
| JP | 2006-516445 A | 7/2007 |
| JP | 2007-520306 | 7/2007 |
| KR | 100944676 B1 | 3/2010 |
| WO | WO-9014796 | 12/1990 |
| WO | WO-9205740 | 4/1992 |
| WO | WO-9222252 | 12/1992 |

| | | |
|---|---|---|
| WO | WO-9321844 | 11/1993 |
| WO | WO-94/01158 A1 | 1/1994 |
| WO | WO-94/01199 A2 | 1/1994 |
| WO | WO-9424948 | 11/1994 |
| WO | WO-96/32882 A1 | 10/1996 |
| WO | WO-97/09934 A1 | 3/1997 |
| WO | WO-98/11830 | 3/1998 |
| WO | WO-99/13779 A2 | 3/1999 |
| WO | WO-00/02488 | 1/2000 |
| WO | WO-02/072188 | 9/2002 |
| WO | WO-2004/069300 | 8/2004 |
| WO | WO-2004/069400 A1 | 8/2004 |
| WO | WO-2004/071612 | 8/2004 |
| WO | WO-2005/074364 | 8/2005 |
| WO | WO-2006/054170 | 5/2006 |
| WO | WO-2007010391 | 1/2007 |
| WO | WO-2009/023866 A1 | 2/2009 |
| WO | WO-2009/046356 A1 | 4/2009 |

OTHER PUBLICATIONS

U.S. Appl. No. 11/791,448, Shimon Eckhouse.
U.S. Appl. No. 11/471,537, Lindenbaum et al.
U.S. Appl. No. 10/616,887, Lindenbaum et al.
U.S. Appl. No. 10/543,654, Eckhouse et al.
Article entitled "The Mechanism of Blood Vessel Closure by High Frequency Electrocoagulation" by Bernard Sigel and Marvin R. Dunn, Surgery Gynecology & Obstetrics, Oct. 1965, vol. 121, No. 4, pp. 823-831.
Article entitled "Repair of small blood vessels with the Neodymium-YAG laser: A preliminary report" by K.K. Jain and W. Gorisch, Surgery, vol. 85, No. 6, pp. 684-688.
International Search Report in co-pending application No. PCT/IL04/000100 (1 page).
About AVD; copyright (2002) Advanced Vascular Dynamics (1 page).
Overview of CompressAR(R) copyright 2002 Advanced Vascular Dynamics (1 page).
"Vascular closure devices for immediate sheath removal after coronary interventions: luxury or necessity"; Silber; http://www.sigmund-silber.com/publ/84/Silber84.htm (Sep. 16, 2005) (12 pages).
Abbott Vascular Devices—ProStar XL 10 product literature (1 page).
International Search Report and Written Opinion for PCT/IB2005/003491, filed Nov. 21, 2005.
U.S. Appl. No. 60/935,484, filed Aug. 15, 2007, Mizrahi et al.
U.S. Appl. No. 60/960,604, filed Oct. 5, 2007, Mizrahi et al.
U.S. Appl. No. 61/006,926, filed Feb. 6, 2008, Mizrahi et al.
U.S. Appl. No. 09/598,232, filed Jun. 21, 2000, Zucker.
Sigel et al., "The Mechanism of Blood Vessel Closure by High Frequency Electrocoagulation", Surgery Gynecology & Obstetrics; (Oct. 1965); vol. 121, No. 4; (pp. 823-831).
K.K. Jain, et al., "Repair of small blood vessels with the Neodymium-YAG laser: A preliminary report", Surgery, vol. 85, No. 6; (1979) (pp. 684-688).
S. Silber, et al., "Vascular Closure Devices for Immediate Sheath Removal after Coronary Interventions: Luxury or Necessity?", ISBN 0-683-30729-0, Handbook of Coronary Stents, 3. ed.; (2000); pp. 147-151.
International Search Report in co-pending application No. PCT/IL04/00100; Dated: Oct. 15, 2004.
Angio-Seal™, 111, 2002, STS Platform Design.
European Search Report in co-pending application No. 02703826.4; Dated: Feb. 6, 2009.
European Search Report in co-pending application No. 99929684.1; Dated: Apr. 6, 2004.
International Search Report in co-pending application No. PCT/IL05/00122; Dated: Dec. 30, 2005.
International Search Report in co-pending application No. PCT/IL02/00200; Dated: Jul. 31, 2002.
International Search Report in co-pending application No. PCT/IL97/00309; Dated: Feb. 3, 1998.
International Search Report in co-pending application No. PCT/IL99/00384; Dated: Nov. 9, 1999.
International Search Report in co-pending application No. PCT/US08/73402; Dated: Oct. 22, 2008.
International Search Report in co-pending application No. PCT/US08/78826; Dated: Dec. 29, 2008.
European Search Report in co-pending application No. EP 08798045.4 issued Jul. 27, 2011.
Japanese Office Action in co-pending application No. JP 2007-542157 issued Feb. 1, 2012.
Canadian Office Action in co-pending application No. CA 2,514,865 issued Feb. 7, 2012.
European Office Action in co-pending application No. EP 05 703 165.0 issued Mar. 29, 2010.
European Office Action in co-pending application No. EP 05 703 165.0 issued Dec. 21, 2009.
European Office Action in co-pending application No. EP 04 707 612.0 issued Sep. 7, 2011.
Korean Notice of Grounds for Refusal in co-pending application No. 10- 2003-7012034 issued Dec. 14, 2007.
Korean Notice of Grounds for Refusal in co-pending application No. 10-2003-7012034 issued Jun. 16, 2008.
Korean Notice of Grounds for Refusal in co-pending application No. 10-2003-7012034 issued Feb. 24, 2009.
In the U.S. Patent and Trademark Office, Non-Final Office Action in re: U.S. Appl. No. 11/791,448, dated Feb. 7, 2012, 12 pages.
In the U.S. Patent and Trademark Office, Non-Final Office Action in re: U.S. Appl. No. 10/543,654, dated Aug. 26, 2009, 11 pages.
In the U.S. Patent and Trademark Office, Final Office Action in re: U.S. Appl. No. 10/543,654, dated Jul. 7, 2010, 10 pages.
In the U.S. Patent and Trademark Office, Examiner's Interview Summary in re: U.S. Appl. No. 10/543,654, dated Aug. 10, 2010, 3 pages.
In the U.S. Patent and Trademark Office, Restriction Requirement in re: U.S. Appl. No. 10/543,654, dated Jan. 22, 2009, 6 pages.
In the U.S. Patent and Trademark Office, Non-Final Office Action in re: U.S. Appl. No. 10/543,654, dated Oct. 26, 2009, 12 pages.
In the U.S. Patent and Trademark Office, Final Office Action in re: U.S. Appl. No. 10/543,654, dated Jul. 7, 2010, 11 pages.
In the U.S. Patent and Trademark Office, Examiner Interview Summary in re: U.S. Appl. No. 09/114,817, dated Oct. 20, 1999, 1 page.
In the U.S. Patent and Trademark Office, Non-Final Office Action in re: U.S. Appl. No. 09/114,817, dated Aug. 24, 1999, 5 pages.
In the U.S. Patent and Trademark Office, Examiner;s Interview Summary in re: U.S. Appl. No. 10/288,843, dated Mar. 1, 2005, 1 page.
In the U.S. Patent and Trademark Office, Non-Final Office Action in re: U.S. Appl. No. 10/288,843, dated Jan. 11, 2005, 4 pages.
In the U.S. Patent and Trademark Office, Notice of Allowance in re: U.S. Appl. No. 09/808,630, dated Oct. 6, 2003, 9 pages.
In the U.S. Patent and Trademark Office, Non-Final Office Action in re: U.S. Appl. No. 09/808,630, dated Sep. 17, 2003, 1 page.
In the U.S. Patent and Trademark Office, Non-Final Office Action in re: U.S. Appl. No. 09/808,630, dated Nov. 25, 2002, 5 pages.
In the U.S. Patent and Trademark Office, Final Office Action in re: U.S. Appl. No. 11/797,294, dated Jul. 26, 2011, 17 pages.
In the U.S. Patent and Trademark Office, Examiner's Interview Summary in re: U.S. Appl. No. 11/797,294, dated Jun. 17, 2010, 4 pages.
In the U.S. Patent and Trademark Office, Notice of Allowance in re: U.S. Appl. No. 09/114,817 dated Dec. 16, 1999, 5 pages.
In the U.S. Patent and Trademark Office, Restriction Requirement in re: U.S. Appl. No. 09/598,232, dated Jun. 5, 2002, 4 pages.
In the U.S. Patent and Trademark Office, Non-Final Office Action in re: U.S. Appl. No. 09/598,232, dated Jul. 16, 2002, 7 pages.
In the U.S. Patent and Trademark Office, Notice of Allowance in re: U.S. Appl. No. 10/288,843, dated Jul. 6, 2005, 6 pages.
In the U.S. Patent and Trademark Office, Non-Final Office Action in re: U.S. Appl. No. 09/808,630, dated Aug. 18, 2003, 5 pages.
In the U.S. Patent and Trademark Office, Restriction Requirement in re: U.S. Appl. No. 09/808,630, dated Jun. 26, 2002, 4 pages.
In the U.S. Patent and Trademark Office, Final Office Action in re: U.S. Appl. No. 08/715,160, dated Jul. 9, 1997, 7 pages.
In the U.S. Patent and Trademark Office, Non-Final Office Action in re: U.S. Appl. No. 08/715,160, dated Feb. 26, 1997, 6 pages.
In the U.S. Patent and Trademark Office, Notice of Allowance in re: U.S. Appl. No. 08/715,160, dated Oct. 2, 1997, 7 pages.

In the U.S. Patent and Trademark Office, Examiner's Interview Summary in re: U.S. Appl. No. 08/715,160, dated Sep. 29, 1997, 6 pages.
In the U.S. Patent and Trademark Office, Non-Final Office Action in re: U.S. Appl. No. 11/471,537, dated Sep. 4, 2008, 6 pages.
In the U.S. Patent and Trademark Office, Non-Final Office Action in re: U.S. Appl. No. 11/797,294, dated Nov. 13, 2008, 12 pages.
In the U.S. Patent and Trademark Office, Final Office Action in re: U.S. Appl. No. 11/797,294, dated Jul. 7, 2009, 12 pages.
In the U.S. Patent and Trademark Office, Non-Final Office Action in re: U.S. Appl. No. 11/797,294, dated Jan. 15, 2010, 12 pages.
In the U.S. Patent and Trademark Office, Final Office Action in re: U.S. Appl. No. 11/797,294, dated Aug. 24, 2010, 12 pages.
In the U.S. Patent and Trademark Office, Non-Final Office Action in re: U.S. Appl. No. 11/797,294, dated Feb. 25, 2011, 2010, 16 pages.
In the U.S. Patent and Trademark Office, Non-Final Office Action in re: U.S. Appl. No. 13/302,6621 dated Mar. 12, 2012, 15 pages.
In the U.S. Patent and Trademark Office, Examiner's Interview Summary in re: U.S. Appl. No. 10/358,130, dated Dec. 7, 2005, 1 page.
In the U.S. Patent and Trademark Office, Non-Final Office Action in re: U.S. Appl. No. 10/616,887, dated Aug. 24, 2005, 7 pages.
In the U.S. Patent and Trademark Office, Final Office Action in re: U.S. Appl. No. 10/616,887, dated May 22, 2006, 7 pages.
In the U.S. Patent and Trademark Office, Notice of Allowance in re: U.S. Appl. No. 10/616,887, dated Jan. 24, 2007, 8 pages.
In the U.S. Patent and Trademark Office, Examiner's Interview Summary in re: U.S. Appl. No. 10/616,887, dated Jun. 26, 2006, 3 pages.
In the U.S. Patent and Trademark Office, Examiner's Interview Summary in re: U.S. Appl. No. 10/616,887, dated Mar. 1, 2006, 3 pages.
In the U.S. Patent and Trademark Office, Restriction Requirement in re: U.S. Appl. No. 10/616,887, dated May 31, 2005, 5 pages.
In the U.S. Patent and Trademark Office, Restriction Requirement in re: U.S. Appl. No. 12/192,911, dated Sep. 13, 2011, 11 pages.
In the U.S. Patent and Trademark Office, Restriction Requirement in re: U.S. Appl. No. 12/245,569, dated Apr. 14, 2011, 9 pages.
In the U.S. Patent and Trademark Office, Non-Final Office Action in re: U.S. Appl. No. 12/245,569, dated Jul. 14, 2011, 9 pages.
In the U.S. Patent and Trademark Office, Final Office Action in re: U.S. Appl. No. 12/245,569, dated Nov. 30, 2011, 8 pages.
In the U.S. Patent and Trademark Office, Non-Final Office Action in re: U.S. Appl. No. 12/192,911, dated Apr. 26, 2012, 28 pages.
European Search Report in co-pending application No. EP 08836162 Issued May 10, 2012.

* cited by examiner

TECHNIQUES FOR HEAT-TREATING VARICOSE VEINS

FIELD OF THE INVENTION

The present invention relates generally to treating a varicose vein, and specifically to methods and apparatus for shrinking and occluding a varicose vein by applying heat thereto.

BACKGROUND OF THE INVENTION

Varicose veins are dilated and tortuous veins, typically superficial veins of the leg. Varicosity is generally caused by an absence or weakness of valves that normally prevent the backward flow of blood away from the heart, or by weaknesses in the vein walls that cause blood to pool.

Techniques for treating varicose veins include surgery and sclerotherapy. Sclerotherapy is the injection directly into the vein of a solution that irritates the lining of the vein, causing it to swell and the blood to clot. Surgical techniques include making two incisions in the vein, one at the ankle and one at the groin. An elongate stripper instrument is then inserted through the ankle incision and passed through the vein to the groin, where a cup is attached to the distal end of the stripper. The stripper is then pulled down the leg, causing the cup to tear out the vein. Newer surgical techniques include damaging an inner endothelial surface of the vein with laser, electric, or radiofrequency (RF) energy.

U.S. Pat. Nos. 6,689,126 and 6,398,780 to Farley et al., which are incorporated herein by reference, describe a catheter including a plurality of primary leads for delivering energy for ligating a hollow anatomical structure. High frequency energy is applied from the leads to create a heating effect in the surrounding tissue of the anatomical structure. Where the hollow anatomical structure is a vein, energy is applied until the diameter of the vein is reduced to the point where the vein is occluded. In one embodiment, a balloon is inflated to occlude the structure before the application of energy. Where the structure is a vein, the inflated balloon obstructs blood flow and facilitates the infusion of saline, medication, or a high-impedance fluid to the vein in order to reduce the occurrence of coagulation and to improve the heating of the vein by the catheter.

U.S. Pat. No. 6,322,559 to Daulton et al., which is incorporated herein by reference, describes an electrode catheter including a coil located at its distal working end. The coil produces an RF field which heats the surrounding venous tissue and causes a reduction in the diameter of the vein. In some embodiments, the catheter includes a balloon that is inflated to engage the coil and occlude the vein. As RF energy is applied, the vein becomes heated and begins to shrink. Occluding the blood flow in the vein with the inflated balloon is described as being able to reduce the effect of blood flow carrying heat away from the treatment site in contact with the electrodes, and to shield blood from heat during treatment, to avoid thrombus formation.

U.S. Pat. Nos. 6,179,832 and 6,682,526 to Jones et al., which are incorporated herein by reference, describe a catheter including a first plurality of expandable leads and a second plurality of expandable leads that are separate and longitudinally spaced-apart from the first plurality. The leads deliver radio frequency (RF) energy, microwave energy, or thermal energy to a hollow anatomical structure, such as vein, fallopian tube, hemorrhoid, or esophageal varix, in order to ligate the structure.

U.S. Pat. No. 6,033,398 to Farley et al., which is incorporated herein by reference, describes a catheter adapted to introduce electrodes into a vein for a minimally invasive treatment of venous insufficiency by the application of energy to cause selective heating of the vein. The catheter is positioned within the vein to be treated, and the electrodes on the catheter are moved toward one side of the vein. RF energy is applied in a directional manner from the electrodes at the working end of the catheter to cause localized heating and corresponding shrinkage of the adjacent venous tissue, which may include commissures, leaflets and ostia. Alternatively, the electrodes can be wires located along or embedded in the surface of the working end of the catheter, in which case the wires generate heat when suitable energy is applied. For example, the wires may be formed of a resistive material and may heat up when electricity is conducted through them. Fluoroscopy or ultrasound may be used to detect shrinkage of the vein. After treating one section of the vein, the catheter can be repositioned to place the electrodes to treat different sections of the vein until, as described, all desired venous valves are repaired and rendered functionally competent.

U.S. Pat. No. 6,071,277 to Farley et al., which is incorporated herein by reference, describes a catheter adapted to deliver an electrode within a hollow anatomical structure for a minimally invasive treatment which reduces the size of the structure. The catheter is introduced and positioned within a section of the hollow anatomical structure to be treated. The electrode radiates high frequency energy, and the surrounding tissue of the hollow anatomical structure becomes heated and begins to shrink. The catheter includes a controllable member for limiting the amount of shrinkage. The temperature of the surrounding hollow anatomical structure can be monitored while the electrode radiates high frequency energy. After treating one section of the hollow anatomical structure, the catheter and electrodes can be repositioned intraluminally to treat different sections of the hollow anatomical structure.

U.S. Pat. No. 6,402,745 to Wilk, which is incorporated herein by reference, describes an intravenous surgical instrument for treating a blood vessel, such as a varicose vein. The instrument comprises an inner shaft or post and an outer sheath. At a distal end of the inner post a spring-tail or whip-like electrode is disposed substantially in a sagittal plane, or one perpendicular to a longitudinal axis of the shaft. Following insertion into the vessel, the distal end of the shaft is protruded from the sheath, and the sheath, post, and electrode are simultaneously withdrawn from the vessel, with a relative rotatory motion being imparted to the electrode. A current flow is preferably simultaneously imposed across the electrode into an inner surface of the surrounding vessel, facilitating damaging of the vessel inner surface and collapse of the vessel.

U.S. Pat. No. 4,869,248 to Narula, which is incorporated herein by reference, describes a thermal ablation catheter for microtransection or macrotransection of conduction paths within the heart. The catheter includes a resistive heating element at its distal end for highly localized treatment. The heating element includes a resistive wire loop connected to an external power source, and has a prescribed shape to insure that the wire loop is approximately perpendicular to the surface to be treated.

U.S. Pat. No. 6,712,806 to St. Germain et al., which is incorporated herein by reference, describes a method for increasing cerebral blood flow. A catheter is inserted into the descending aorta, the catheter having a proximal region, a distal region, and at least one expandable member mounted on the distal region. The expandable member is positioned downstream from the takeoff of the brachiocephalic artery.

The expandable member is expanded to at least partially obstruct blood flow in the aorta. The expandable member is then cycled between greater and lesser obstruction of blood flow. Renal ischemia and lower limb ischemia is described as being avoided in this manner.

U.S. Pat. No. 6,712,804 to Roue et al., which is incorporated herein by reference, describes a closure catheter, for closing a tissue opening such as an atrial septal defect, patent foramen ovale, or the left atrial appendage of the heart. The closure catheter carries a plurality of tissue anchors, which may be deployed into tissue surrounding the opening, and used to draw the opening closed.

U.S. Pat. No. 6,451,007 to Koop et al., which is incorporated herein by reference, describes techniques for selective heating of subsurface structures in material such as tissue, including a cooling device for thermally quenching or removing heat from the top surface of tissue during or just after delivering pulsed energy to target or subsurface structures or tissue. An embodiment uses dynamic cooling, to quench the thermal energy conducted from the targeted structure into surrounding tissue.

U.S. Pat. No. 6,712,815 to Sampson et al., which is incorporated herein by reference, describes ablation techniques for closing veins, for treatment of venous insufficiency disease. The apparatus includes a catheter proportioned for insertion into a vein, a pair of inflatable balloons spaced apart on the catheter body, and an ablation electrode array disposed between the balloons. The catheter is introduced into the vein to be treated and the balloons are distended. Blood is flushed and aspirated from the site between the balloons. RF power is applied to the electrode array, causing scarring of the vessel walls and eventual sealing of the vein.

U.S. Pat. No. 6,676,657 to Wood, which is incorporated herein by reference, describes techniques for occluding the lumen of a hollow organ by delivering radiofrequency energy to the inner wall of the organ. Radiofrequency electrodes are described that expand, in a deployed condition, to contact the walls of the organ. In some embodiments, the electrodes substantially conform to the inner wall to enhance therapeutic contact. Methods are also disclosed for using these electrodes to totally or partially occlude a lumen, or to remove or reduce a total or partial occlusion of a lumen. For some applications, the electrodes include an expandable distal end that is retracted, or collapsed into a compact configuration, in the non-deployed position and is expanded in the deployed position. The expandable distal end can assume the form of a plurality of struts that extend longitudinally with respect to the conductive member, and the struts are attached to the conductive member such that longitudinal movement of the conductive member moves the struts between the retracted and expanded positions. For example, the struts are attached at a first end to the conductive member and are fixed at a second end around the conductive member, such that longitudinal movement of the conductive member (for example retraction of the conductive member toward a sheath) forces the struts into the expanded position. The device can include a sheath around the catheter, to which the proximal end of the struts is attached. As the distal end of the conductive member is pulled toward the sheath, the struts are compressed and expand to the deployed position in contact with the wall of the lumen.

U.S. Pat. No. 6,772,013 to Ingle et al., which is incorporated herein by reference, describes techniques for treating urinary incontinence generally relying on energy delivered to a patient's own pelvic support tissue to selectively contract or shrink at least a portion of that pelvic support tissue so as to reposition the bladder. Techniques are described for applying gentle resistive heating of these and other tissues to cause them to contract without imposing significant injury on the surrounding tissue structures.

U.S. Pat. No. 6,768,086 to Sullivan et al., which is incorporated herein by reference, describes a warming blanket having a temperature sensing element for sensing the temperature of the warming blanket.

US Patent Application Publication 2004/0199155 to Mollenauer, which is incorporated herein by reference, describes techniques for the treatment of various incompetent valves and sphincters throughout the body. The catheters provide for location of a heating element or other tissue necrosing tool in the lumen of the vessel controlled by the valve, at or near the base of the valve (but not on the valve itself). Additionally, the catheters include balloons for locating and anchoring the distal section of the catheter within the lumen, such that the heating element is positioned near the base of the valve, in contact with lumenal tissue at the base of the valve. The catheters also include suction ports on the distal end of the catheter which can be operated to size or draw down the vessel to the diameter of the catheter, so that the vessel walls are in contact with the heating elements. The heating elements comprise resistive heating elements, electrodes, RF electrodes, ultrasonic heat sources, LEDs and other light or laser sources, or other suitable heating mechanisms. Where the heating elements are resistive heating elements, the electrical wires comprise a ground wire and a hot wire, and, as described, while a minor amount of current may pass through the body to ground, the bulk heating of the venous tissue is caused by conductive heating from the heating elements which are in turn heated due to resistance of the elements and the passage of current through the elements. Appropriate materials for the resistive heating elements include nichrome and nickel-titanium alloys such as nitinol.

US Patent Application Publication 2004/0010298 to Altshuler et al., which is incorporated herein by reference, describes techniques for selectively heating blood vessels in a patient's skin to effect a desired dermatological (medical or cosmetic) treatment. For shallow vessels, particularly plexus vessels and superficial vessels/veins, radiation is applied to the vessels involved in the treatment which includes substantial radiation in a blue band of approximately 380-450 nm. The treatment may be enhanced by applying pressure and/or cooling to the patient's skin which, among other things, removes blood from blood vessels above blood vessels for which treatment is desired.

US Patent Application Publication 2003/0109869 to Shadduck, which is incorporated herein by reference, describes a medical instrument that utilizes electrical energy delivery between first and second opposing polarity electrodes in an interior bore of a working end to cause vaporization of an inflowing fluid media. The vaporization and expansion of the fluid media creates pressure gradients in the working end that causes heated vapor to propagate distally from the working end. The propagation or jetting of the vapor media is used to controllably cause thermal effects in endoluminal environments. The instrument and method can be used to shrink and occlude blood vessels in a treatment for varicose veins. US Patent Application Publications 2004/0199226 and 2004/0068306 to Shadduck, which are incorporated herein by reference, describe similar techniques for treating tissue with heat.

US Patent Application Publication 2003/0120256 to Lary et al., which is incorporated herein by reference, describes apparatus for sclerosing the wall of a varicose vein, which includes an inner tube having an expandable balloon at its distal end, an intermediate tube slidably disposed over the inner tube and having a fluid outlet at its distal end and a plunger at its proximal end, and an outer tube through which the plunger is movable. Methods of using the apparatus include deploying the inner and intermediate tubes in the vessel to be sclerosed, inflating the balloon, filling the outer tube with sclerosing agent and moving the plunger from the distal end of the outer tube toward the proximal end.

US Patent Application Publication 2004/0092913 to Hennings et al., which is incorporated herein by reference, describes techniques for treating varicose veins or the greater saphenous vein. The techniques include the use of infrared laser radiation in the region of 1.2 to 1.8 um in a manner from inside the vessel such that the endothelial cells of the vessel wall are damaged, collagen fibers in the vessel wall are heated to the point where they permanently contract, and the vessel is occluded and ultimately resorbed. The device includes a laser delivered via a fiber optic catheter that may have frosted or diffusing fiber tips. A motorized pull back device is used, and a thermal sensor may be used to help control the power required to maintain the proper treatment temperature. A controlled cooling system is described which allows a predetermined amount of cryogenic fluid to be dispensed from an on-board fluid reservoir or from an external/line source. In an embodiment, the cooling device is computer controlled, to provide spurts or squirts of cryogenic fluid at a predetermined rate or for a predetermined duration.

US Patent Application Publication 2002/0072761 to Abrams et al., which is incorporated herein by reference, describes surgical techniques for achieving a desired configuration of one or more anatomical structures by suction or inflation, and then by optionally deploying a stabilizing or fastening agent or holding device, for example a helical staple, to stabilize the anatomical structure in the desired configuration. Aspects of the invention can be used in the treatment of incontinence, coronary artery blockage, tubal ligation, vasectomy, treatment of morbid obesity, and treatment of varicose veins. For some applications, a wire is deployed within the lumen of the fallopian tube or other anatomical structure, to sufficiently damage the tissue prior to placement of the helical staple or other stabilizing or fastening agent. Tissue damage in this manner is described as tending to promote more rapid tissue growth, better ensuring closure of the anatomical structure. For some applications, the wire is a resistive wire that is heated and thus causes thermal damage. Alternatively or additionally, the wire is an abrasive wire that damages the tissue by direct abrasive contact.

PCT Publication WO 04/071612 to Slater et al., which is incorporated herein by reference, describes techniques for treating the interior of a blood vessel, including a variety of catheter designs, methods and apparatus for occluding a blood vessel, including an inflatable occlusion balloon.

SUMMARY OF THE INVENTION

In some embodiments of the present invention, apparatus for treating a varicose vein comprises a catheter adapted to be inserted into the vein; a heating element, adapted to be coupled to the catheter, and to be placed in contact with at least a portion of a wall of the vein; and a control unit, adapted to drive the heating element to apply to the vein heat sufficient to shrink the vein. Sufficient heating of the vein damages endothelial cells and typically causes permanent contraction of collagen fibers in the wall of the vein, partially or entirely occluding the vein. Such treatment is typically performed for medical or cosmetic purposes. For some applications, the heating element comprises a resistive heating element, and the control unit is adapted to drive a current through the resistive heating element.

In some embodiments of the present invention, the resistive heating element is coupled to the catheter in a vicinity of a distal end thereof, and typically has a length of between about 2 mm and about 8 mm, e.g., between about 3 mm and about 5 mm, or between about 5 mm and about 8 mm. The catheter is typically inserted into a proximal incision of the vein, and advanced to a distal location in the vein, typically using an introducer inserted over a guidewire. The catheter is then withdrawn while the resistive heating element heats the wall of the vein.

In other embodiments of the present invention, the resistive heating element is highly elongated, typically having a length greater than 10% of the length of the segment of the vein to be shrunk, such as greater than 50% or 100% of the length of the vein segment. For example, the length of the resistive heating element may be approximately 100% of the length of the vein segment. The catheter, with the heating element coupled thereto, is inserted into a proximal incision of the vein, and advanced to a distal location in the vein, typically using an introducer inserted over a guidewire. For applications in which the length of the heating element is approximately 100% of the length of the vein segment, the heating element simultaneously heats the wall of the entire vein segment, while the catheter remains in place. Upon completion of the heating, the catheter is withdrawn. Such simultaneous heating generally reduces the duration of the procedure, and generally ensures uniform heating of the entire segment of the vein. Typically, the heat application itself takes about 1 to about 30 seconds, e.g., about 5 to about 20 seconds. Because the catheter remains in place during heating, the uniformity of the heat application does not rely on the ability of the physician to withdraw the catheter at a generally constant rate during heat application.

In some embodiments of the present invention, the apparatus further comprises a cooling element adapted to be applied to an external surface of the skin above a vicinity of the heating element. For some applications, an external coupling element, such as a wire, couples the cooling element to a portion of the apparatus that remains inside the body, such as the distal portion of the catheter and/or introducer. As the catheter is withdrawn from the vein, the wire pulls the cooling element, so that the cooling element remains above the vicinity of the heating element throughout the procedure. For some applications, the cooling element is adapted to apply pressure to the vein via the skin so as to push blood out of the vein ahead of or at the portion of the vein to which the heating element is currently applying heat.

There is therefore provided, in accordance with an embodiment of the present invention, apparatus for treating a varicose vein of a subject, including:

a catheter having a distal end and a proximal portion, the distal end adapted to be placed within the varicose vein, and the proximal portion adapted to remain outside a body of the subject;

a heating element, disposed at the distal end of the catheter, and adapted to heat the vein;

a cooling element, adapted to be applied to an external surface of skin above a vicinity of the heating element, and to apply cooling to the skin; and a coupling element, adapted to remain outside the body, and to couple the cooling element to the proximal portion of the catheter.

There is further provided, in accordance with an embodiment of the present invention, apparatus for treating a varicose vein, including:

an elongated heating element, adapted to be placed in the varicose vein, the heating element having an active heating portion having a longitudinal length greater than 4 cm; and a control unit, adapted to drive the heating element to apply heat to the vein simultaneously from the entire active heating portion.

In an embodiment, the heating element includes a resistive heating element.

There is also provided, in accordance with an embodiment of the present invention, apparatus for treating a varicose vein, including:

a resistive heating element, adapted to be placed within the varicose vein; and a control unit, coupled to the heating element, and adapted to:

apply a current to the heating element that resistively heats the heating element, and measure a temperature of the heating element by measuring a change in resistivity of the heating element to the current.

In an embodiment, the control unit is adapted to regulate application of the current responsive to the measured temperature.

There is additionally provided, in accordance with an embodiment of the present invention, a method for treating a varicose vein, including:

inserting an elongated heating element into a segment of the varicose vein, the heating element having an active heating portion having a longitudinal length greater than 50% of a length of the segment; and driving the heating element to apply heat to the segment simultaneously from the entire active heating portion.

In an embodiment, the heating element includes a resistive heating element, and wherein inserting the heating element includes inserting the resistive heating element into the segment.

The present invention will be more fully understood from the following detailed description of embodiments thereof, taken together with the drawings, in which:

DETAILED DESCRIPTION OF EMBODIMENTS

Figure 1:
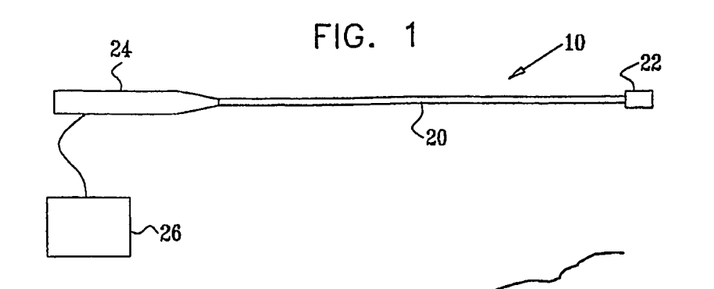
FIG. 1 is a schematic illustration of a system for treating a varicose vein, in accordance with an embodiment of the present invention.

FIG. 1 is a schematic illustration of a system 10 for treating a varicose vein of a subject, in accordance with an embodiment of the present invention. System 10 comprises a catheter 20 adapted to be inserted into the varicose vein; a heating element 22, which typically but not necessarily comprises a resistive heating element, adapted to be coupled to catheter 20; and a control handle 24, coupled to a proximal end of catheter 20. System 10 further comprises a control unit 26, coupled to handle 24, and adapted to drive heating element 22 to apply heat to the vein. For applications in which heating element 22 comprises a resistive heating element, control unit 26 is adapted to drive a current through the resistive heating element.

Figures 2, 3A, 3B:
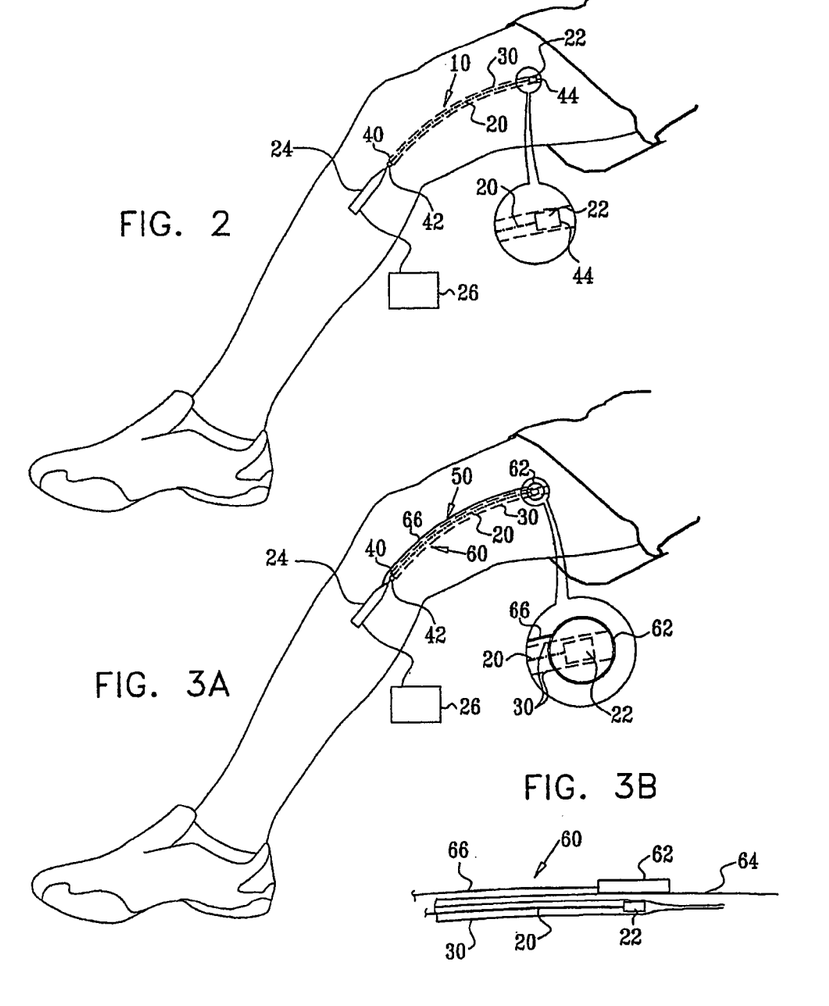
FIG. 2 is a schematic illustration of the system of FIG. 1 during treatment of a segment of a varicose vein, in accordance with an embodiment of the present invention.
FIG. 3A is a schematic illustration of another system for treating a varicose vein.
FIG. 3B is a schematic cross-sectional view of a distal portion of the system, in accordance with an embodiment of the present invention.

FIG. 2 is a schematic illustration of system 10 during treatment of a segment 30 of a varicose vein, in accordance with an embodiment of the present invention. In this embodiment, heating element 22 is coupled to a distal end of catheter 20, and typically has a length of between about 2 mm and about 8 mm, such as between 3.5 and 4.5 mm. Although for illustrative purposes segment 30 is shown in an upper leg of the subject, the scope of the invention includes other locations in the leg and the body.

During a procedure performed using system 10, an incision 40 is made at a proximal end 42 of vein segment 30. A guidewire (not shown) is inserted into the segment until a distal end of the guidewire reaches a distal end 44 of vein segment 30, typically about 1 to about 2 cm from the saphenous-femoral junction. An introducer (not shown), comprising a tube, is inserted into the segment over the guidewire, and the guidewire is removed. Catheter 20 is inserted through the introducer until the catheter reaches distal end 44 of vein segment 30. Heating element 22 is placed in a vicinity of at least a portion of a wall of the vein (e.g., adjacent thereto or in contact therewith). Control unit 26 drives heating element 22 to apply to the vein heat that is sufficient to shrink the vein. Catheter 20 is withdrawn at a controlled rate while heating element 22 heats the wall of the vein. As appropriate, the withdrawal may be accomplished manually or by means of an automatic withdrawal unit (not shown), which may be powered electrically, hydraulically, using compressed gas, or using another power source. Sufficient heating of the vein damages endothelial cells and typically causes permanent contraction of collagen fibers in the wall of the vein, partially or entirely occluding the vein.

For applications in which heating element 22 comprises a resistive heating element, control unit 26 drives either a DC current or an AC current through the heating element. When driving an AC current, the control unit typically drives the current at greater than about 1 kHz or greater than about 100 kHz, e.g., at about 400 kHz. For some applications, the control unit drives the heating element to release energy within the vein at a rate of greater than 20 W. For some applications, the control unit drives the heating element to apply energy to the vein at a rate sufficient to shrink a length of at least 40 cm of tissue of the varicose vein in less than 60 seconds. For some applications, the control unit drives the heating element to simultaneously apply energy to at least 18 mm2 of tissue, at a flux of at least 50 W/cm2.

Reference is now made to FIGS. 3A and 3B. FIG. 3A is a schematic illustration of a system 50 for treating a varicose vein of a subject, and FIG. 3B is a schematic cross-sectional view of a distal portion of system 50, in accordance with an embodiment of the present invention. System 50 is generally similar to system 10, described hereinabove with reference to FIGS. 1 and 2, except that system 50 additionally comprises a cooling device 60. Cooling device 60 comprises a cooling element 62, adapted to be applied to an external surface of skin 64 above a vicinity of heating element 22. Cooling element 62 may comprise, for example, a Peltier device, an ice pack, or a coolant sprayer (e.g., a cryogenic liquid sprayer).

For some applications, control unit 26 regulates the application of the cooling, such as in order to achieve a desired temperature. For example, cooling device 60 may comprise a temperature sensor.

For some applications, cooling device 66 additionally comprises an external coupling element 66. Coupling element 66 may be resilient (i.e., bendable but generally able to return to its original form), or non-resilient (for example, stiff, or completely flexible). Coupling element 66 couples cooling element 62 to a portion of system 50 that remains inside the body, such as a distal portion of catheter 20, typically via control handle 24, and/or the introducer. For example, coupling element 66 may be attached to control handle 24 and configured to be generally aligned in parallel with catheter 20, in the absence of any external forces. As catheter 20 is withdrawn from the vein, coupling element 66 pulls cooling element 62 along skin 64 in alignment with heating element 22. As a result, cooling element 62 remains above the vicinity of heating element 22 throughout the procedure, thereby continuously cooling skin 64 and other tissue in the vicinity of the heating element during the procedure.

For some applications, cooling element 62 is adapted to apply pressure to the vein via skin 64 so as to push blood out of the vein ahead of the portion of the vein to which heating element 22 is currently applying heat. In an embodiment, cooling element 62 comprises a flat or slightly curved planar portion, at least 3 cm2 in size. Typically, the planar portion is placed against the skin and used to facilitate the pushing of the blood out of the vein. Alternatively, system 50 comprises the planar portion, coupled to coupling element 66, and does not comprise cooling element 62. In this embodiment, the planar portion is typically but not necessarily used to facilitate the pushing of the blood out of the vein.

For some applications, system 50 comprises coupling element 66, but does not comprise cooling element 62 or the planar portion. For these applications, coupling element 66 is typically used to facilitate a determination of the location of the distal portion of catheter 20.

Figure 4:
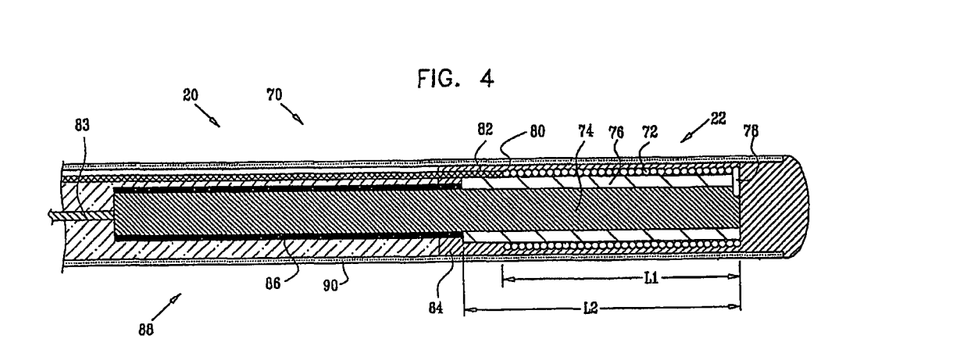
FIG. 4 is a schematic cross-sectional illustration of a distal portion of a catheter for treating a varicose vein, in accordance with an embodiment of the present invention.

Reference is now made to FIG. 4, which is a schematic cross-sectional illustration of a distal portion 70 of catheter 20, in accordance with an embodiment of the present invention. In this embodiment, heating element 22 comprises a resistive heating element, which comprises a wire coil 72, comprising, for example, a nickel chromium alloy. For some applications, the longitudinal length L1 of coil 72 is between about 2 and about 8 mm, e.g., about 6 and about 8 mm, such as about 7 mm. (The term "longitudinal length," as used herein, including in the claims, means a length along a longitudinal axis of the catheter or heating element, and does not mean a length of the wire of the coil.) For some applications, the wire has a diameter of between about 0.06 and about 0.1 mm, such as about 0.08 mm, and a length of between about 10 and about 15 cm, such as about 12 cm. Coil 72 is wrapped around a conductive rod 74 having a non-conductive coating 76, which coating typically coats a length L2 of the rod of between about 1 mm and 5 mm (such as about 2.5 mm) greater than length L1. For some applications, rod 74 comprises stainless steel, and has a diameter of between about 0.4 and about 0.5 mm, such as about 0.45 mm. For some applications, coating 76 comprises a ceramic coating, such as Duceram™ Plus (DeguDent GmbH, Germany), which is oven-cured onto rod 74. One end 78 of coil 72 is welded to and in electrical contact with rod 74, and the other end 80 of the coil is coupled to a first conductive wire 82. A second conductive wire 83 is coupled to a proximal end of rod 74. A dielectric filler 84 surrounds coil 72. Heat-shrink insulation 86 surrounds a more proximal portion 88 of rod 74 that is not surrounded by coil 72. A tube 90, such as a stainless steel tube, surrounds the entire catheter.

Typically, the actual length of the wire that forms coil 72 is between about 10 cm and about 25 cm, e.g., about 15 to about 20 cm. Alternatively, the length of the wire that forms coil 72 is greater than 25 cm. Although the wire may be coated with an insulating substance, it is typically uncoated. Typically, at least one loop of coil 72 touches an adjacent loop of coil. The surface area at which the two adjacent loops touch is typically small, whereby only a small amount of current is "shorted" between the adjacent coils, relative to the amount of current that travels through the length of the wire. For some applications, coil 72 is tightly looped, and all or nearly all of the loops are in contact with adjacent loops. In each case, typically, this contact is over a very small surface area.

For some applications, the length of the wire that forms coil 72 is less than 10 cm, and/or none of the loops touch adjacent loops.

Figure 5:
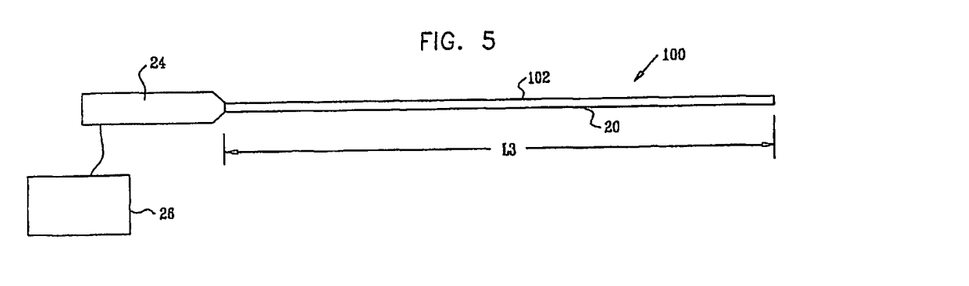
FIG. 5 is a schematic illustration of yet another system for treating a varicose vein, in accordance with an embodiment of the present invention.

Reference is now made to FIG. 5, which is a schematic illustration of a system 100 for treating a varicose vein of a subject, in accordance with an embodiment of the present invention. System 100 is generally similar to system 10, described hereinabove with reference to FIGS. 1 and 2, except that, instead of heating element 22, system 100 comprises a highly-elongated heating element, such as a highly-elongated resistive heating element 102. A length L3 of heating element 102 is typically greater than about 10% of the length of the vein segment being shrunk, such as greater than about 50% of the length of the vein segment, or greater than 100% of the length of the vein segment. In an embodiment, length L3 is equal to the length of the vein segment being shrunk. Typically, length L3 is greater than about 30 cm, such as greater than about 40 cm. For typical varicose vein treatments, length L3 is less than 50 cm.

For some applications, heating element 102 has a construction similar to that of the resistive element described hereinabove with reference to FIG. 4, with appropriate adjustments of the dimensions of the components.

The first portion of a procedure performed using system 100 is generally similar to that of a procedure performed using system 10, as described hereinabove with reference to FIG. 2. An incision is made at a proximal end of a vein segment, and a guidewire is inserted into the segment until a distal end of the guidewire reaches a distal end of the segment. An introducer, comprising a tube, is inserted into the segment over the guidewire, and the guidewire is removed. Catheter 20 is inserted through the introducer until the catheter reaches the distal end of the vein segment. However, unlike in the procedure performed using system 10, for applications in which length L3 of heating element 102 is approximately 100% of the length of the vein segment, control unit 26 drives a current through heating element 102 so that the heating element simultaneously heats the wall of the entire vein segment, while catheter 20 and heating element 102 remain in place. Upon completion of the heating, catheter 20 is withdrawn. Such simultaneous heating generally reduces the duration of the procedure, and provides generally uniform heating of the entire segment of the vein. Typically, the heat application itself takes about 1 to about 30 seconds, e.g., about 5 to about 20 seconds. Because the catheter remains in place during heating, the uniformity of the heat application does not rely on the ability of the physician to withdraw the catheter at a generally constant rate during heat application.

For applications in which length L3 of heating element 102 is between 10% and 100% of the length of the vein segment, the heating element is positioned at a distal end of the vein segment, and heated so as to shrink at least 10% of the vein segment (e.g., about 50 to about 100% of the vein segment). The heating element is then partially withdrawn, such that the distal end of the heating element is positioned at the most proximal point of the vein that was shrunk. The heating element is heated a second time, typically completing the shrinking of the entire vein segment.

In an embodiment of the present invention in which heating element 22 or 102 comprises a resistive heating element, control unit 26 is adapted to measure a temperature of the heating element by measuring a change in resistivity of the heating element to the current driven therethrough by control unit 26. For some applications, control unit 26 is adapted to regulate an amount of current driven through the heating element responsively to the measured temperature.

In an embodiment of the present invention in which heating element 22 or 102 comprises a resistive heating element, during insertion of the heating element into the vein, ultrasound is used to determine that the distal end of the heating element has been positioned at a desired location. The coil of the heating element serves as an ultrasound reflector that is sufficiently reflective of ultrasound so as to facilitate locating of the heating element within the varicose vein during the procedure. The need for a separate ultrasound reflector is thus obviated.

In an embodiment of the present invention, catheter 20 comprises an expanding element, such as a balloon or an umbrella-shaped element, positioned proximal to heating element 22. As the catheter is withdrawn during a procedure, the expanding element pushes blood proximally from the vein, reducing the amount of blood in a vicinity of the heating element.

In an embodiment of the present invention, catheter 20 comprises a cooling element, such as a Peltier device, in a vicinity of the tip of the catheter. For some applications, control unit 26 regulates the application of cooling, such as in order to achieve a desired temperature. For example, catheter 20 may comprise a temperature sensor in the vicinity of the tip thereof.

For some applications, techniques described in one or more of the patents or patent application publications described in the Background of the Invention are used in combination with techniques described herein.

Although the heating techniques described herein have been described as useful for occluding varicose veins, these techniques may also be used to (a) reduce a diameter of a vein without occluding the vein, for example to treat a venous valve, or (b) treat another body lumen, such as a lumen described in the references cited in the Background of the Invention of the present patent application.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a vein of a subject, comprising: a catheter having a distal end and a proximal portion, the distal end adapted to be placed within the varicose vein, and the proximal portion adapted to remain outside a body of the subject; a heating element, disposed at the distal end of the catheter, and adapted to heat the vein; a cooling element, adapted to be applied to an external surface of skin-above a vicinity of the heating element, and to apply cooling to the skin; and a coupling element, adapted to remain outside the body, and to couple the cooling element to the proximal portion of the catheter.

2. The apparatus of claim 1, wherein the heating element applies heat to the vein for about 1-30 seconds.

3. The apparatus of claim 1, wherein the coupling element is a wire.

4. The apparatus of claim 1, wherein the cooling element is adapted to apply pressure to the vein via the skin.

5. The apparatus of claim 1, wherein the heating element is a resistive heating element.

6. The apparatus of claim 1, further comprising a control unit driving current at greater than about 1kHz.

7. The apparatus of claim 1, wherein the heating element applies energy at a flux of at least $50W/cm^2$.

8. The apparatus of claim 1, wherein the cooling element is selected from the group consisting of: a Peltier device, an ice pack, and a coolant sprayer.

9. The apparatus of claim 1, wherein the cooling element further comprises a temperature sensor.

10. The apparatus of claim 1, wherein the coupling element is configured to be generally aligned in parallel with the catheter.

11. The apparatus of claim 1, wherein the cooling element further comprises a flat or slightly curved planar portion.

12. The apparatus of claim 1, wherein the heating element has a diameter of between about 0.06 and about 0.1 mm.

13. The apparatus of claim 1, wherein the heating element is wrapped around a conductive rod having a non-conductive coating.

14. The apparatus of claim 1, wherein the vein is a varicose vein.

* * * * *